(12) United States Patent
Baldwin et al.

(10) Patent No.: US 10,915,703 B2
(45) Date of Patent: Feb. 9, 2021

(54) VALIDATING AN XML DOCUMENT

(71) Applicant: International Business Machines Corporation, Armonk, NY (US)

(72) Inventors: Timothy J. Baldwin, Swanmore (GB); Duncan G. Clark, Yateley (GB); Xin Peng Liu, Beijing (CN); Xi Ning Wang, Beijing (CN); Liang Xue, Beijing (CN); Yu Chen Zhou, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/512,825

(22) Filed: Jul. 16, 2019

(65) Prior Publication Data

US 2020/0012716 A1 Jan. 9, 2020

Related U.S. Application Data

(63) Continuation of application No. 14/830,491, filed on Aug. 19, 2015, now Pat. No. 10,372,809, which is a
(Continued)

(30) Foreign Application Priority Data

Jul. 24, 2008 (CN) .......................... 2008 1 0134072

(51) Int. Cl.
*G06F 40/18* (2020.01)
*G06F 40/14* (2020.01)
(Continued)

(52) U.S. Cl.
CPC .............. *G06F 40/18* (2020.01); *G06F 40/14* (2020.01); *G06F 40/226* (2020.01);
(Continued)

(58) Field of Classification Search
CPC ............. G06F 17/2247; G06F 17/2725; G06F 17/2872; G06F 17/272; G06F 17/24;
(Continued)

(56) References Cited

U.S. PATENT DOCUMENTS 7,036,072 B1 * 4/2006 Sulistio .................. G06F 40/14
715/205
9,146,908 B2 9/2015 Baldwin et al.
(Continued)

FOREIGN PATENT DOCUMENTS

| CN | 1704932 A | 12/2005 |
| CN | 101634982 A | 1/2010 |
| JP | 11-250483 A | 3/2001 |

OTHER PUBLICATIONS

Leigh Dodds, Schematron: Validating XML Using XSLT, Website/page, Printed from website on Oct. 6, 2008, pp. 1-21, Bath University, Published at: http://www.1dodds.com/papers/schematron_xsltuk.html.
(Continued)

*Primary Examiner* — Quoc A Tran
(74) *Attorney, Agent, or Firm* — Christopher M. Pignato

(57) ABSTRACT

At least one XML document to be validated is parsed, and XML data in the at least one XML document is represented as data objects in at least one data object model in a memory. At least one rule document is parsed and a rule object model that includes rule objects is created in the memory. At least part of the data objects are extracted from the at least one data object model and at least part of rule objects are extracted from the rule object model. Partial validation is performed in a corresponding execution context that validates the extracted at least part of the data objects based upon the extracted at least part of the rule objects.

21 Claims, 6 Drawing Sheets

Related U.S. Application Data continuation of application No. 12/507,261, filed on Jul. 22, 2009, now Pat. No. 9,146,908.

(51) Int. Cl.

| | | |
|---|---|---|
| *G06F 40/226* | (2020.01) | |
| *G06F 16/25* | (2019.01) | |
| *G06F 16/957* | (2019.01) | |
| *G16C 20/70* | (2019.01) | |
| *G06F 16/84* | (2019.01) | |
| *G06Q 10/10* | (2012.01) | |
| *G06Q 10/06* | (2012.01) | |
| *G06F 40/55* | (2020.01) | |
| *G06F 40/154* | (2020.01) | |
| *G06F 40/166* | (2020.01) | |
| *G06F 40/221* | (2020.01) | |
| *G06F 17/00* | (2019.01) | |

(52) U.S. Cl.
CPC ............ *G06F 16/258* (2019.01); *G06F 16/86* (2019.01); *G06F 16/9577* (2019.01); *G06F 40/154* (2020.01); *G06F 40/166* (2020.01); *G06F 40/221* (2020.01); *G06F 40/55* (2020.01); *G06Q 10/06* (2013.01); *G06Q 10/10* (2013.01); *G16C 20/70* (2019.02)

(58) Field of Classification Search
CPC ........ G06F 19/707; G06F 16/86; G06F 40/14; G06F 40/226; G06F 40/55; G06F 40/154; G06F 40/166; G06F 40/221; G06F 16/258; G06Q 10/10; G06Q 10/06
See application file for complete search history.

(56) References Cited

U.S. PATENT DOCUMENTS

| | | |
|---|---|---|
| 2004/0021679 A1 | 2/2004 | Chapman et al. |
| 2005/0039124 A1 | 2/2005 | Chu et al. |
| 2005/0097455 A1 | 5/2005 | Zhou et al. |
| 2005/0246159 A1 | 11/2005 | Perla et al. |
| 2005/0278270 A1 | 12/2005 | Carr et al. |
| 2006/0117307 A1 | 6/2006 | Averbuch et al. |
| 2008/0017722 A1 | 1/2008 | Snyder |
| 2008/0082959 A1 | 4/2008 | Fowler |
| 2008/0104579 A1 | 5/2008 | Hartmann |
| 2008/0120316 A1* | 5/2008 | Vion-Dury .............. G06F 40/14 |
| 2009/0265378 A1 | 10/2009 | Dahl et al. |
| 2012/0216111 A1 | 8/2012 | Sulistio et al. |
| 2015/0356069 A1 | 12/2015 | Baldwin et al. |
| 2019/0340229 A1 | 11/2019 | Baldwin |

OTHER PUBLICATIONS

Eric Armstrong, A Simple Collaboration System (Proposal), Website/page, Printed from website on Oct. 6, 2008, pp. 1-13, Treelight Software, Published at: .ttp://www.treelight.com/software/collaboration/SimpleSystem.html.

Author Unknown, Topologi Schema Documentation Tool, Website/page, Printed from website on Oct. 6, 2008, pp. 1-3, Topologi Pty. Limited, NSW, Australia, Published at. http://www.topologi.com.

Author Unknown, Program (xml.php), Website/page, Printed from website on Oct. 6, 2008, pp. 1-191, World Wide Web Conference 2007, Canada, Published at: http://www2007.org/program/xml.php.

Rick Jelliffe, The W3C XML Schema Specification in Context, Website/page, Printed from website on Oct. 6, 2008, pp. 1-4, O'Reilly Media, Inc., Published at: http://www.xml.com/pub/a/2001/01/10/schemasincontext.html? page=5.

Eddie Robertsson, An Introduction to Schematron, Website/page, Printed from website on Oct. 6, 2008, pp. 1-10, O'Reilly Media, Inc., Published at: http://www.xml.com/lpt/a/1318.

Chimezie Ogbuji, Validating XML with Schematron, Website/page, Printed from website on Oct. 6, 2008, pp. 1-6, O'Reilly Media, Inc., Published at: http://www.xml.com/lpt/a/687.

Rick Jelliffe, The Schematron Assertion Language 1.6, The Schematron software project, Oct. 1, 2002, pp. 1-32, Academia Sinica Computing Centre, Published at: http://xml.ascc.net/resource/schematron/Schematron2000.html.

Quoc A. Tran, Examiner, United States Patent and Trademark Office, Office Action for U.S. Appl. No. 12/507,261, dated Apr. 10, 2012, pp. 1-29, Alexandria, VA, USA.

Quoc A. Tran, Examiner, United States Patent and Trademark Office, Office Action for U.S. Appl. No. 12/507,261, dated Dec. 14, 2012, pp. 1-21, Alexandria, VA, USA.

Quoc A. Tran, Examiner, United States Patent and Trademark Office, Office Action for U.S. Appl. No. 12/507,261, dated Aug. 22, 2013, pp. 1-23, Alexandria, VA, USA.

Quoc A. Tran, Examiner, United States Patent and Trademark Office, Office Action for U.S. Appl. No. 12/507,261, dated Jan. 14, 2014, pp. 1-20, Alexandria, VA, USA.

Quoc A. Tran, Examiner, United States Patent and Trademark Office, Office Action for U.S. Appl. No. 12/507,261, dated Jul. 31, 2014, pp. 1-31, Alexandria, VA, USA.

Quoc A. Tran, Examiner, United States Patent and Trademark Office, Notice of Allowance for U.S. Appl. No. 12/507,261, dated May 20, 2015, pp. 1-18, Alexandria, VA, USA.

Quoc A. Tran, Examiner, United States Patent and Trademark Office, Office Action for U.S. Appl. No. 14/830,491, dated Aug. 28, 2017, pp. 1-33, Alexandria, VA, USA.

Quoc A. Tran, Examiner, United States Patent and Trademark Office, Office Action for U.S. Appl. No. 14/830,491, dated Feb. 28, 2018, pp. 1-36, Alexandria, VA, USA.

Quoc A. Tran, Examiner, United States Patent and Trademark Office, Advisory Action for U.S. Appl. No. 14/830,491, dated May 8, 2018, pp. 1-5, Alexandria, VA, USA.

Quoc A. Tran, Examiner, United States Patent and Trademark Office, Office Action for U.S. Appl. No. 14/830,491, dated Sep. 20, 2018, pp. 1-16, Alexandria, VA, USA.

Quoc A. Tran, Examiner, United States Patent and Trademark Office, Notice of Allowance for U.S. Appl. No. 14/830,491, dated Mar. 27, 2019, pp. 1-6, Alexandria, VA, USA.

"Schematron" A language for making assertions about patterns found in XML documents, web archive dated May 12, 2008, 2 pages, <https://web.archive.org/web/20080512085819/http://www.schematron.com/>.

Hinkelman, Scott, "Business Information Conformance Statements for Java", IBM, Date Posted Jan. 22, 2004, 1 page, <https://web.archive.org/web/20080515164011/http://www.alphaworks.ibm.com/tech/biics4j>.

* cited by examiner

| | |
|---|---|
| ⊞ ◇ schema | Schema (id=35) |
| ⊞ ▦ patterns | ArrayList<E> (id=60) |
| ⊟ ▦ elementData | Object[10] (id=73) |
| ⊟ ▲ [0] | Pattern (id=79) |
| ⊞ ◇ lets | LinkedHashMap<K,V> (id=83) |
| ⊞ ▦ name | "Basic validation" |
| ⊞ ▦ paras | ArrayList<E> (id=86) |
| ▦ prefix | null |
| ⊟ ▦ rules | ArrayList<E> (id=87) |
| ⊟ ▦ elementData | Object[10] (id=93) |
| ⊟ ▲ [0] | Rule (id=95) |
| ▦ _abstract | false |
| ⊟ ▦ assertions | ArrayList<E> (id=99) |
| ⊟ ▦ elementData | Object[10] (id=104) |
| ⊟ ▲ [0] | Assertion (id=109) |
| ⊞ ▦ contents | ArrayList<E> (id=112) |
| ⊞ ▦ diagnosticIdList | ArrayList<E> (id=111) |
| ⊞ ▦ test | "(@sex='Male' and @title='Mr') or (@sex='Female' and ..." |
| | |
| ⊞ ▦ targetNamespaceURI | "http://purl.oclc.org/dsdl/schematron" |
| ⊞ ▦ title | "Employee and Asset" |
| ⊞ ▦ uriPrefixMap | HashMap<K,V> (id=65) |

FIG. 4

VALIDATING AN XML DOCUMENT

BACKGROUND

The present invention relates to computer document processing technology, and particularly relates to a method and system for validating XML documents.

Standard Generalized Markup Language (SGML) is an information management standard adopted by the International Organization for Standardization (ISO) for providing platform- and application software independent documents. In a document, format, index and links are maintained. SGML provides a mechanism similar to a grammar for defining document structure and tags. The tags are used for representing format of different documents.

Extensible Markup Language (XML) is a standard language suggested by W3C. It is a condensed format of SGML. XML provides more flexibility for web developers and designers to create customized marks, organize and represent information. XML is used to exchange documents and data for Service-Oriented Architecture (SOA) and Web services. One of the advantages of XML as a format for data exchange is the standardization of validation technology.

Many XML application developers expect that there is a method to guarantee that all XML instances comply with some specific rules, such as guaranteed validation processing. Thus, many people directly seek help from schema language, e.g. DTD, W3C XML Schema (WXS) and RELAX NG. The effort may be performed by applying some rules to XML instances.

Usually, validation technology includes a grammar based validation method. As an alternative, Schematron is a structural validation language. Schematron allows to directly express rules without the need to create a whole grammar base. Tree patterns, defined as XPath expressions, are used to make assertions, and provide user-centric reports about XML documents. Expressing validation rules using patterns is often easier than defining the same rule using a content model. Tree patterns are collected together to form a Schematron schema. Schematron is a useful tool for other schema languages. Schematron is a useful tool to apply rules for an XML document or validate with rules. Schematron is flexible, and may be used to express different rules. Its expressing capability may be more suitable than other schema languages (e.g., DTD, W3C XML Schema (WXS), and RELAX NG).

Efforts were made by the industry and academia to implement Schematron. FIG. 1 shows a widely used and referenced Schematron implementation method. One may refer to http://www.schematron.com, which is a typical implementation method with open source software, and is frequently used by various projects. Schematron uses XML Stylesheet Language For Transformation (XSLT), and defines a schema language which, when transformed through a meta-style sheet (i.e. a style sheet which generates other style sheets), produces XSLT validation document. FIG. 1 shows the process.

The web site http://www.ldodds.com/papers/schematron_xsltuk.html also introduced Schematron and other implementations based on XSLT.

Furthermore, the Community-driven Systems Management in Open Source (COSMOS) project aims to provide inter-operable tools for system management. The COSMOS Resource Modeling sub-project aims to provide support for building a common model to represent the information being shared in a system management scenario. The project is using SML and Schematron as the XML schema language to define this common model. It uses the XSLT based approach and skeleton1-5.xsl (http://xml.ascc.net/schematron/1.5/) reference implementation to extract the Schematron from the schema.

SUMMARY

The above examples are all based on an XSLT approach. According to embodiments of the present invention, a new method and system for validating an XML document is provided. The method comprises parsing at least one XML document to be validated, and representing XML data in the at least one XML document as data objects in at least one data object model in a memory; parsing at least one rule document and creating a rule object model comprising rule objects in the memory; extracting at least part of the data objects from the at least one data object model and extracting at least part of the rule objects from the rule object model; and performing validation in a corresponding execution context for the extracted at least part of the data objects based upon the extracted at least part of the rule objects.

According to another embodiment of the present invention, a system for validating a XML document is provided. The system comprises a memory; a data parsing module configured to parse at least one XML document to be validated and to represent XML data in the at least one XML document as data objects in at least one data object model in the memory; a rule parsing module configured to parse at least one rule document and create a rule object model comprising rule objects in the memory; an extracting module configured to extract at least part of the data objects from the at least one data object model and extract at least part of the rule objects from the rule object model; and a validation module configured to perform validation in a corresponding execution context for the extracted at least part of the data objects based upon the extracted at least part of the rule objects.

According to another embodiment of the present invention, the at least one rule document comprises at least one Schematron document, and the rule objects in the rule object model maintain a hierarchical relationship corresponding to elements in the at least one Schematron document. Each element in the at least one XML document is mapped to a data object in the at least one data object model, the data objects maintain a hierarchical relationship corresponding to elements in the at least one XML document to be validated.

Where, at least part of rule objects are extracted from the rule object model according to predefined rule extraction criteria. At least part of data objects are extracted from the data object model according to predefined data extraction criteria.

According to a further embodiment of the present invention, the method further comprises: generating an execution context for at least one rule object of the extracted at least part of the rule objects, registering the execution context to a context registry, and performing validation for the at least one rule object in the execution context. An execution context for one rule object of the extracted at least part of the rule objects may be searched from a context registry, and validation may be performed for the one rule object in the execution context.

BRIEF DESCRIPTION OF THE DRAWINGS

FIG. 4 illustrates a rule object model in memory according to an embodiment of the present invention.

DETAILED DESCRIPTION

Figure 1:
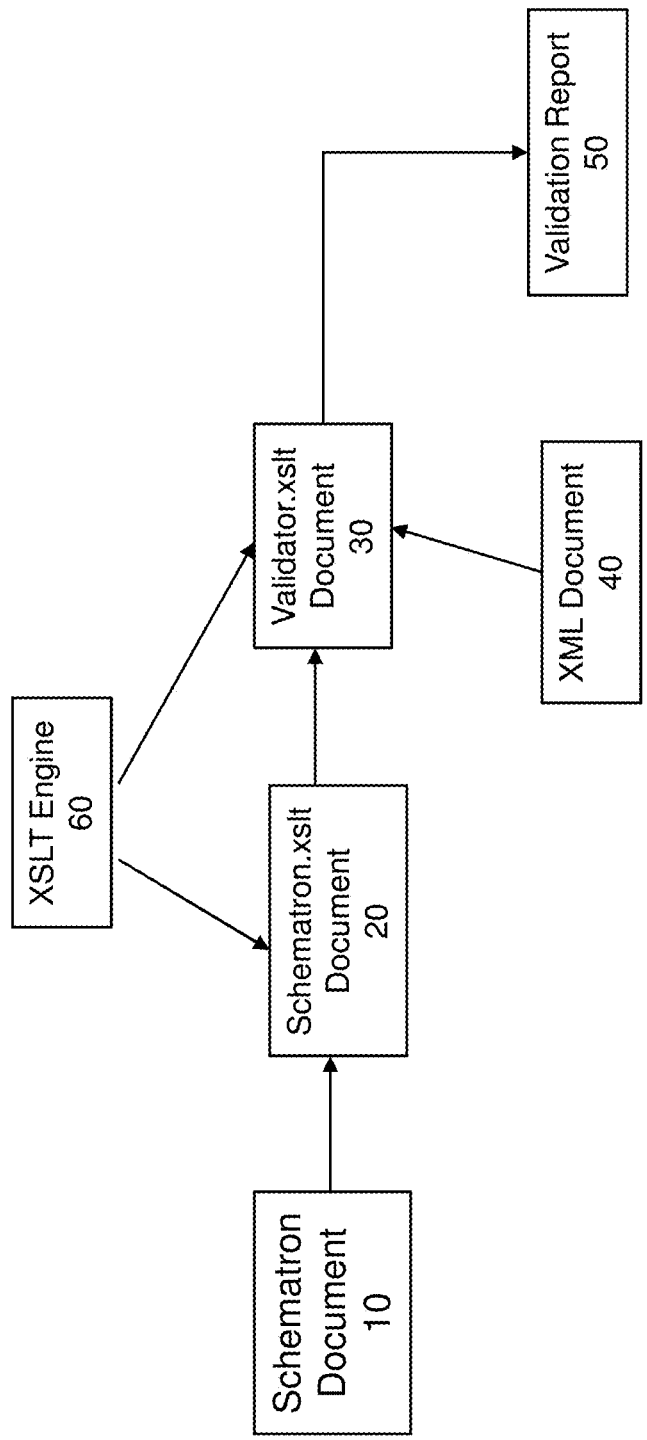
FIG. 1 illustrates an XSLT based XML document validation method with Schematron.

FIG. 1 illustrates an XSLT based XML document validation method with Schematron. The examples described in the background part are based on XSLT for XML document validation which has the following limitations. XSLT based Schematron validation will necessarily include the following two-round processes, because the XSLT engine will process documents with XLST grammar and cannot directly process Schematron documents, only after a Schematron document is transformed into an executable XSLT document can the XSLT engine continue to execute the new transformed XSLT document. In FIG. 1, Schematron document 10 as an XML rule document will first be transformed into Schematron.xslt document 20. The content in this new XSLT document is the Schematron-defined rule.

The XML document validation process with Schematron is divided into two procedures. The first procedure is transforming a Schematron rule document into an intermediate document, i.e. Validator.xslt document 30 by executing Schematron.xslt document 20 in an XSLT engine 60. The second procedure is executing the Validator.xslt document 30 in the XSLT engine 60 to perform validation for XML document 40 to generate a final validation report 50.

A performance issue will be caused by the two rounds of XSLT transformation. A Schematron schema is transformed into an equivalent XSLT document, and is commonly implemented as a meta-style sheet, called skeleton. This skeleton is applied to the Schematron schema and the resulting XSLT is in turn applied to the XML instance document. Because there are two rounds of transformations based on XSLT in the validation process, the performance often becomes a critical issue especially in some environments requiring real-time processing, such as registry and repository with a large number of concurrent operations by end users and applications.

Such an XSLT based validation method lacks shareable rule context. The contexts of each rule are not shareable, so that many nodes are traversed more than once in the validation process. It is also another critical issue for performance.

It is difficult to achieve fail-fast validation with Schematron. Fail-fast refers to a lightweight form of fault tolerance, where an application or system service terminates itself immediately upon encountering an error. Schematron validation based on XSLT transformation makes it difficult to achieve fail-fast implementation due to the nature of XSLT.

Such an XSLT based method has matching problems generated by XSLT. Such problems usually exist in XSLT based implementations. For example, when in the same pattern, some rule context scopes overlap with each other, it will cause more than one rule to be satisfied and get triggered. Using an XSLT based implementation, each rule is represented as a template; but for XSLT 1.0, if multiple templates are matched at the same time, only one with the highest priority will be called, with the others being ignored. XSLT 2.0 has the feature to do "match-next", but still cannot completely solve the problem. This defect makes a gap between the Schematron specification and XSLT capability.

Such an XSLT based method makes it difficult to support partial validation with fine grained assertions in a Schematron document. Using an XSLT approach, the smallest unit of the rule container to be selected in a Schematron document is a "phase" element, where users or applications could not select a finer grained unit, such as a rule or an assertion, for validation. It may cause a problem when there is a requirement to validate XML documents with only a subset of a phase, for example where a user selected rules or assertions, and rules or assertions for a specific version or a section of a standards specification such as WS-I BP, etc., let alone the other advanced features for more flexible validation are used.

Figure 2:
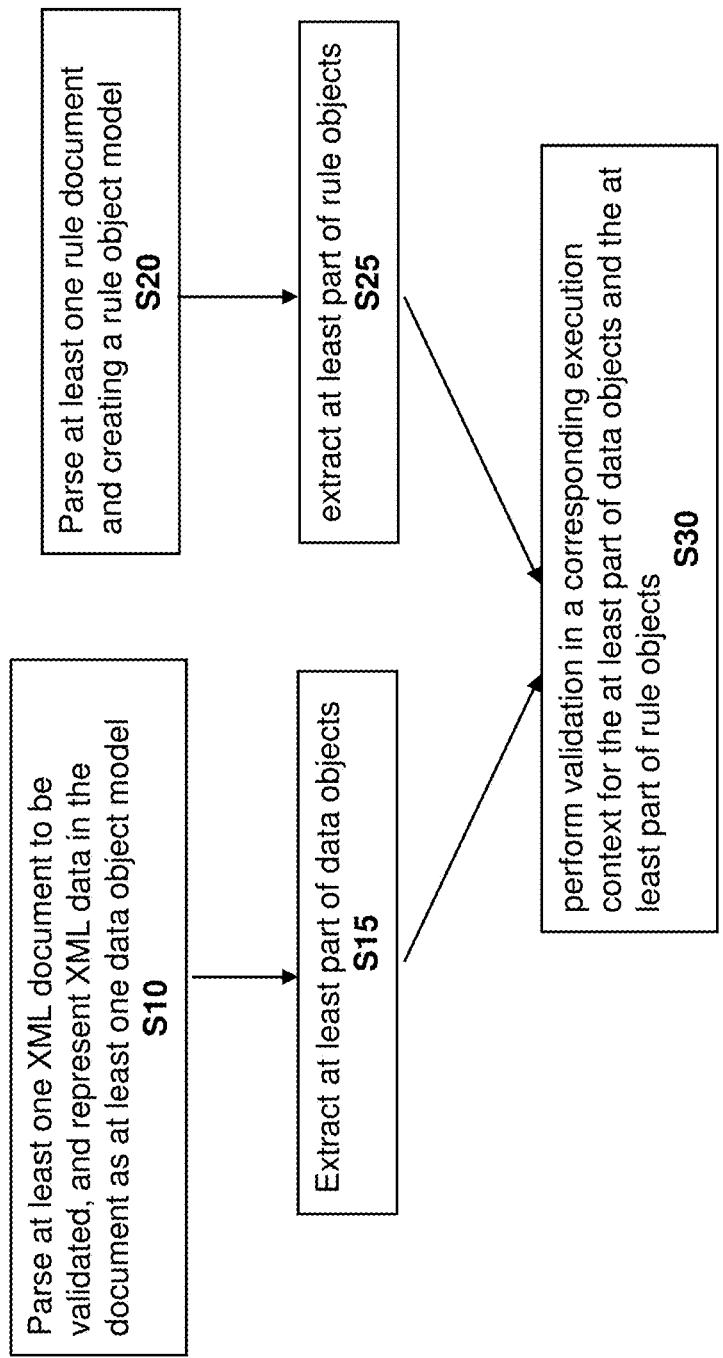
FIG. 2 illustrates a flowchart for XML document validation method according to an embodiment of the present invention.

FIG. 2 illustrates a flowchart of an example XML document validation method according to an embodiment of the present invention. The method includes the following steps. At step S10, parse at least one XML document to be validated, and represent XML data in the document as at least one data object model. The data object model may be created and stored in memory, or may be created and stored with other technology of hardware and/or virtual software convenient for access. The data object model may adopt a tree structure, e.g. Document Object Model (DOM). Every element in the XML document may be mapped as a data object in the data object model. The data objects may keep a corresponding relationship with the elements in the XML document to be validated.

At step S20, parse at least one rule document and create a rule object model. The rule object model may be created and stored in memory, or may be created and stored with other technology of hardware and/or virtual software convenient for access.

At step S15, extract at least part of data objects from the data object model. The data object extraction criteria may be predefined, and data objects may be automatically extracted according to the criteria. The data object model may be provided to a user via a user interface. The user may select data objects from the data object model. User defined functions may also be used for extracting data objects.

At step S25, extract at least part of rule objects from the rule object model. The rule object extraction criteria may be predefined, and rule objects may be automatically extracted according to the criteria. The rule object model may be provided to a user via a user interface. The user may select rule objects from the rule object model. User defined functions may also be used for extracting rule objects.

At step S30, perform validation in a corresponding execution context for the at least part of data objects and the at least part of rule objects. The execution context may be predefined, or generated according to a rule object and a data object to be validated. A context registry may be maintained for storing execution contexts for validation. An execution context for an extracted rule object may be searched from the context registry, and validation for the rule object may be performed in the execution context.

According to one embodiment of the present invention, for an XML instance document, validation may be performed using all rules or part of the rules; and all or part of the data in the XML instance document may be validated using all of the rules or part of the rules. After data objects to be validated and rule objects are determined, the validation process executes the rule objects for the data objects to be validated in the corresponding execution context.

According to another embodiment of the present invention, the method further includes: generating an execution context for at least one of the extracted rule objects, and registering the execution context to a context registry, and performing validation for the at least one rule object in the execution context.

According to a further embodiment of the present invention, the data object model and the rule object model may be created in memory. The rule document is a Schematron document, and rule objects in the rule object model maintain a hierarchical relationship corresponding to elements in the Schematron document.

According to a further embodiment of the present invention, the method further includes stopping validation in response to a fail-fast rule being triggered.

Figure 3:
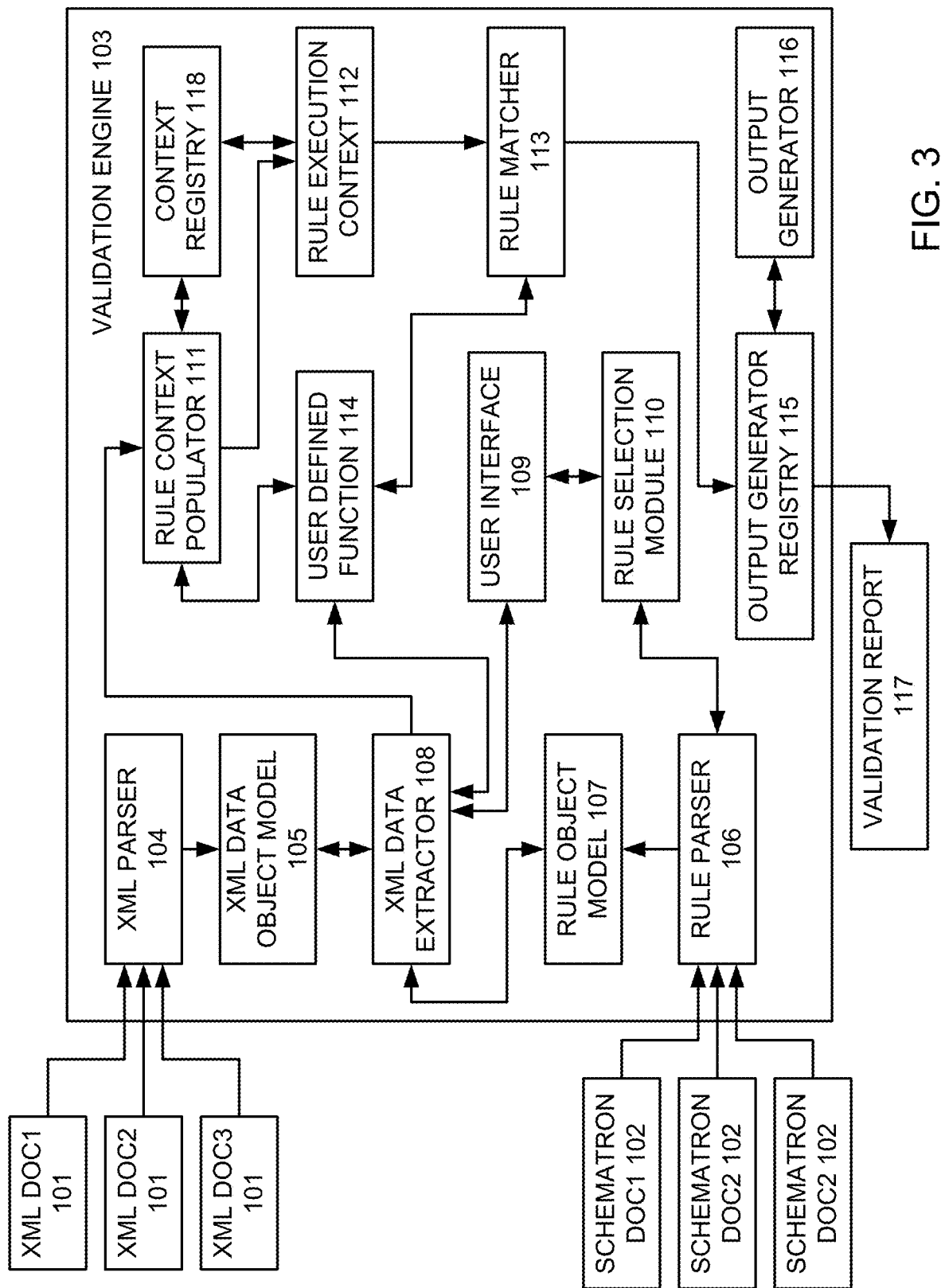
FIG. 3 illustrates a block diagram for XML document validation system according to another embodiment of the present invention.

FIG. 3 illustrates a block diagram for an example XML document validation system according to another embodiment of the present invention. In FIG. 3, the XML document 101 comprises contents to be validated with a rule. For example, the XML instance about a customer's purchase order to be validated is shown as the following.

The data in the above XML instance includes an employee with family name "WEN," given name "Chuan," employee number "SOADC913247," sex "Female," and title "Mr." There are some assets information under the name of this employee.

Schematron document 102 is for storing rules for validating the above XML document. Schematron language allows for expressing rules directly to make sure that all XML instances will follow specific rules. If rules are to be applied to XML document contents or used for checking the document, Schematron may be used. For example, different authors submit documents to a company for publishing a technical document. Editors want to check the submitted documents with a set of rules to make sure that they comply with editing requirements and may be correctly processed by publishing tools.

In Schematron documents, declarations are used for defining various XML vocabularies and may be shared with various XML based applications. The constraints rules include XML Schema-based validation which is strictly a check for format and correctness, but also includes complex application logic for multiple XML documents. For example, the following Schematron document may be used to express the rules to validate the example XML document shown above.

```
<?xml version="1.0" encoding="UTF-8"?>
<employees xmlns="http://example.ibm.com/employee">
   <employee serialNumber="SOADC913247" sex="Female" title= "Mr"
      deptId="SOADC">
      <firstName>Chuan</firstName>
      <lastName>WEN</lastName>
      <assets>
         <asset assetNumber="P2PQH402" capitalizedDate="2008-04-10"
            status="active">
            <complianceInfo>
               <check date="2008-01-10" standard="Sec300" status="passed"/>
               <check date="2008-02-18" standard="Sec400" status="failed"/>
               <check date="2008-03-22" standard="Sec800" status="failed"/>
            </complianceInfo>
            <items>
               <item partNum="001-AA">
                  <productName>PC</productName>
                  <quantity>1</quantity>
                  <price>13000.80</price>
               </item>
               <item partNum="002-BB">
                  <productName>keyboard</productName>
                  <quantity>1</quantity>
                  <price>288.88</price>
               </item>
               <item partNum="003-CC">
                  <productName>Monitor</productName>
                  <quantity>2</quantity>
                  <price>2000</price>
               </item>
            </items>
         </asset>
         <asset assetNumber="A22J7602" capitalizedDate="2008-03-22"
            status="unused">
            <unusedInfo reason="LowerPerformance">
            <detail>
               The performance of this assset is very lower!
            </detail>
            </unusedInfo>
         </asset>
      </assets>
   </employee>
</employees>
```

```xml
<?xml version="1.0" encoding="UTF-8" ?>
<schema xmlns="http://purl.oclc.org/dsdl/schematron">
  <title>Employee and Asset</title>
  <ns uri="http://example.ibm.com/employee" prefix="em" />
  <pattern name="Basic validation">
    <rule context="/em:employees/em:employee">
      <assert
        test="(@sex='Male' and @title='Mr') or (@sex='Female' and (@title='Mrs' or @title='Miss'))">
        The value of title does not match the value of sex.
      </assert>
      <assert test="@serialNumber and @deptId">
        Both serialNumber and deptId must be present.
      </assert>
      <report test="not(starts-with(@serialNumber=@deptId))">
        The serialNumber must starts with the deptId.
      </report>
    </rule>
  </pattern>
  <pattern name="As sets count validation">
    <rule context32 "/em:employees/em:employee/em:assets">
      <assert test="count(em:asset[@status='active']) >= 1">
        Each employee should have at least one asset which status is active.
      </assert>
      <report test="count(em:asset) > 10">
        Each employee should have at most ten assets.
      </report>
    </rule>
  </pattern>
  <pattern name="As set price validation">
    <rule
context="/em:employees/em:employee/em:assets/em:asset[@status='active']/em:items">
      <assert test="em:item">
        Each asset which status is active should have at least one item.
      </assert>
      <report
        test="sum(em:item/em:price/text( )) > 10000">
        For each employee, the sum of price of all the active assets can't be greater than 10000.
      </report>
    </rule>
  </pattern>
  <pattern name="As set advanced validation">
    <rule context="/em:employees/em:employee/em:assets/em:asset[@status='active']">
      <assert test="em:complianceInfo">
        Each active asset must include the compliance check information.
      </assert>
    </rule>
    <rule
context="/em:employees/em:employee/em:assets/em:asset[@status='active']/em:complianceInfo/em:check">
      <report test="@standard='Sec300' and not(@status='passed')">
        If the check standard is 'Sec300', corresponding status must be 'passed'.
      </report>
      <report test="@standard='Sec400' and not(@status='passed' or @status='uncertain')">
        If the check standard is 'Sec400', corresponding status should be 'passed' or 'uncertain'.
      </report>
      <report test="@standard='Sec800' and @status='failed'">
        If the check standard is 'Sec800', and corresponding status is present, the status should be not 'failed'.
      </report>
    </rule>
    <rule context="/em:employees/em:employee/em:assets/em:asset[@status='unused']">
      <assert test="em:unusedInfo">
        The unused assets must include the unused information.
      </assert>
      <assert test="em:unusedInfo/@reason!='' or em:unusedInfo/detail/text( )!=''">
        Asset[serial number: <value-of select="./@assetNumber"/>] is unused, but has not unused reason or detail.
      </assert>
    </rule>
  </pattern>
</schema>
```

The above Schematron document includes rules for validating the above XML document, e.g. the assertion "(@sex='Male' and @title='Mr') or (@sex='Female' and (@title='Mrs' or @title='Miss'))" for validating the title of WEN Chuan in the above XML document is correct or not. If the title is not correct, then output "The value of title does not match the value of sex."

A validation engine 103 performs the structure and content constraints validation for the target XML object model by using a rule object model. The validation engine 103 may include some or all of the following modules. For example, a user defined function 114 or an output generator registry 115 may be included or may not be included.

An XML Parser 104 is used to parse the XML document 101, and may be implemented by using different implementation languages (for example, Java, C #, etc). XML Parser may be implemented as codes for reading a document and parsing its contents. The XML parser 104 reads the XML document 101, provides programmatic access to its XML data, and consequently determines how this data may be accessed or retrieved. Typically, it may be a Document Object Model (DOM) Parser, Streaming API for XML (SAX) Parser, etc.

The XML Parser 104 parses at least one of XML document 1, XML document 2 and/or XML document 3 to be validated, and expresses the XML data as at least one XML data object model. Every element in the XML document is mapped to a data object in the data object model, and the data objects keep hierarchical relationship corresponding to elements in the XML document to be validated.

The XML Parser 104 may parse the XML document 101 to be validated in memory, and store the XML data object model 105 in memory. Thus, matching may be performed by using data object model in memory to do refined matching. Validation for part of the XML document 101 may be performed according to user's selection or predefinition. In other words, validation for part of objects in XML data object model 105 may be performed.

The XML data object model 105, may be a document object model (DOM) in which an XML document is usually modeled as a node-labeled tree. Each element in the document is mapped to a sub tree in the tree, which root node is labeled with the tag of the element.

A rule parser 106 parses at least one rule document 102, e.g. the Schematron document 1, Schematron document 2 and/or Schematron document 3 in FIG. 3, and creates a rule object model 107. The rule object model may be created in memory. The created rule object model 107 may be stored in memory.

The rule parser 106 is used to parse the constraint rules using the extended Schematron language. These constraint rules may be formed as an XML document so that they may be parsed by any XML parser. According to one embodiment of the present invention, the Rule parser 106 is based on the Document Object Model Application Programming Interface (DOM API) to parse the constraint rules document into the rule object model 107 in memory.

In a further embodiment of the present invention, the rule document may be a Schematron document. The rule objects in the rule object model 107 maintain a hierarchical relationship corresponding to elements in the Schematron document. The rule parser 106 parses the Schematron document according to its grammar, and creates a corresponding rule object model in memory. The Schematron document may be an XML document by its nature. The Schematron document may be first parsed with an XML DOM processing mechanism, and then memory objects may be created according to element names in the document. For example, if a parsed XML original name is rule, then a corresponding rule object model may be created. Because the elements in the Schematron document have a hierarchical relationship, the corresponding rule object model in memory will also maintain the corresponding hierarchical relationship.

For example, the rule object model in FIG. 4 may be created from the following

Schematron document.

Schematron Document:

```
<?xml version="1.0" encoding="UTF-8" ?>
<schema xmlns="http://purl.oclc.org/dsdl/schematron">
    <title>Employee and Asset</title>
    <ns uri="http://example.ibm.com/employee" prefix="em" />
    <pattern name="Basic validation">
        <rule context="/em:employees/em:employee">
            <assert test="(@sex='Male' and @title='Mr') or (@sex='Female' and
                (@title='Mrs' or @title='Miss'))">
                The value of title does not match the value of sex.
            </assert>
            <assert test="@serialNumber and @deptId">
                Both serialNumber and deptId must be present.
            </assert>
            <report test="not(starts-with(@serialNumber,@deptId))">
                The serialNumber must starts with the deptId.
            </report>
        </rule>
    </pattern>
    <pattern name="Assets count validation">
        <rule context="/em:employees/em:employee/em:assets">
            <assert test="count(em:asset[@status='active']) >= 1">
                Each employee should have at least one asset which status is active.
            </assert>
            <report test="count(em:asset) > 10">
                Each employee should have at most ten assets.
            </report>
        </rule>
    </pattern>
    <pattern name="Asset price validation">
        <rule
            context="/em:employees/em:employee/em:assets/em:asset[@status='active']/em:items">
            <assert test="em:item">
```

-continued

```
      Each asset which status is active should have at least one item.
    </assert>
    <report
      test="sum(em:item/em:price/text( )) > 10000">
      For each employee, the sum of price of all the active assets can't be greater than
10000.
    </report>
  </rule>
</pattern>
<pattern name="Asset advanced validation">
  <rule context="/em:employees/em:employee/em:assets/em:asset[@status='active']">
    <assert test="em:complianceInfo">
      Each active asset must include the compliance check information.
    </assert>
  </rule>
  <rule
context="/em:employees/em:employee/em:assets/em:asset[@status='active']/em:complianceInfo/
em:check">
    <report test="@standard='Sec300' and not(@status='passed')">
      If the check standard is 'Sec300', corresponding status must be 'passed'.
    </report>
    <report test="@standard='Sec400' and not(@status='passed' or
@status='uncertain')">
      If the check standard is 'Sec400', corresponding status should be 'passed' or
'uncertain'.
    </report>
    <report test="@standard='Sec800' and @status='failed'">
      If the check standard is 'Sec800', and corresponding status is present, the status
should be not 'failed'.
    </report>
  </rule>
  <rule context="/em:employees/em:employee/em:assets/em:asset[@status='unused']">
    <assert test="em:unusedInfo">
      The unused assets must include the unused information.
    </assert>
    <assert test="em:unusedInfo/@reason!=" or em:unusedInfo/detail/text( )!="">
      Asset[serial number: <value-of select="./@assetNumber"/>] is unused, but has
not unused reason or detail.
    </assert>
  </rule>
</pattern>
</schema>
```

The object in the rule object model maintains a corresponding hierarchical relationship with elements in the above Schematron document. For example, the object, schema Schema(id=35), in line 1 of FIG. 4 corresponds to the elements starting from line 2 of the Schematron document, <schema xmlns="http://purLocic.org/dsdl/schematron">. The object in line 4 of FIG. 4, [0] Pattern (id=79), corresponds to the element, <pattern name="Basic validation">, starting from line 5 of the Schematron document. The object in line 11 of FIG. 4, [0] Rule(id=95), corresponds to the element, <rule context="/em:employees/em:employee">, starting from line 6 of the Schematron document. The object in line 15 of FIG. 4, [0] Assertion(id=109), corresponds to the element starting from line 7 of the Schematron document (e.g., <assert test="(@sex='Male' and @title='Mr') or (@sex='Female' and (@title='Mrs' or @title='Miss'))"> The value of title does not match the value of sex. </assert>).

The rule object model 107 may represent an in-memory model of rules, and may be created by the rule parser 106. The core elements include a context element, a rule logic expression, and validation output, etc.

An XML data extractor 108 extracts nodes of XML document object model tree. Xpath is a widely used language for addressing parts of an XML document to extract a data object. Xpath may be used as a stand-alone query language for XML, and may also be used in a host language such as XQuery and XSLT. For example, an XPath query includes a location path and an output expression. The location path is a sequence of location steps that specify the path from the document root to a desired element. The output expression specifies the portions or functions of a matching element that form the results.

A user interact module for data extracting, i.e. a user interface 109, allows the user to select elements to be validated from a target XML document. Samples of such data may be elements of the same type, a sub tree of the whole DOM tree, or a set of elements filtered using XPath pattern, etc. Such information for data selection and/or selected data elements may be passed to a rule selection module 110 for identifying the fine grained units, such as rules or assertions, for partial validation.

The rule selection module 110 interacts with an end user/application (e.g., via the user interface 109) for selecting rules to be used for validation. The information for rule selection may be generated by a user, e.g. a user selection of the rules/assertions to be used directly from UI, or may be automatically generated using the information of data selection from the user interface 109 for data extraction. Additionally, the information for rule selection is passed to the rule parser 106 for generating a rule object model to be used for validation.

A rule context populator 111 is for populating a rule execution context 112 of each rule. These contexts may be shared by multiple rules which have the related execution scope.

The rule execution context 112 provides a concrete execution scope of each rule applied to a XML instance document.

Figure 5:
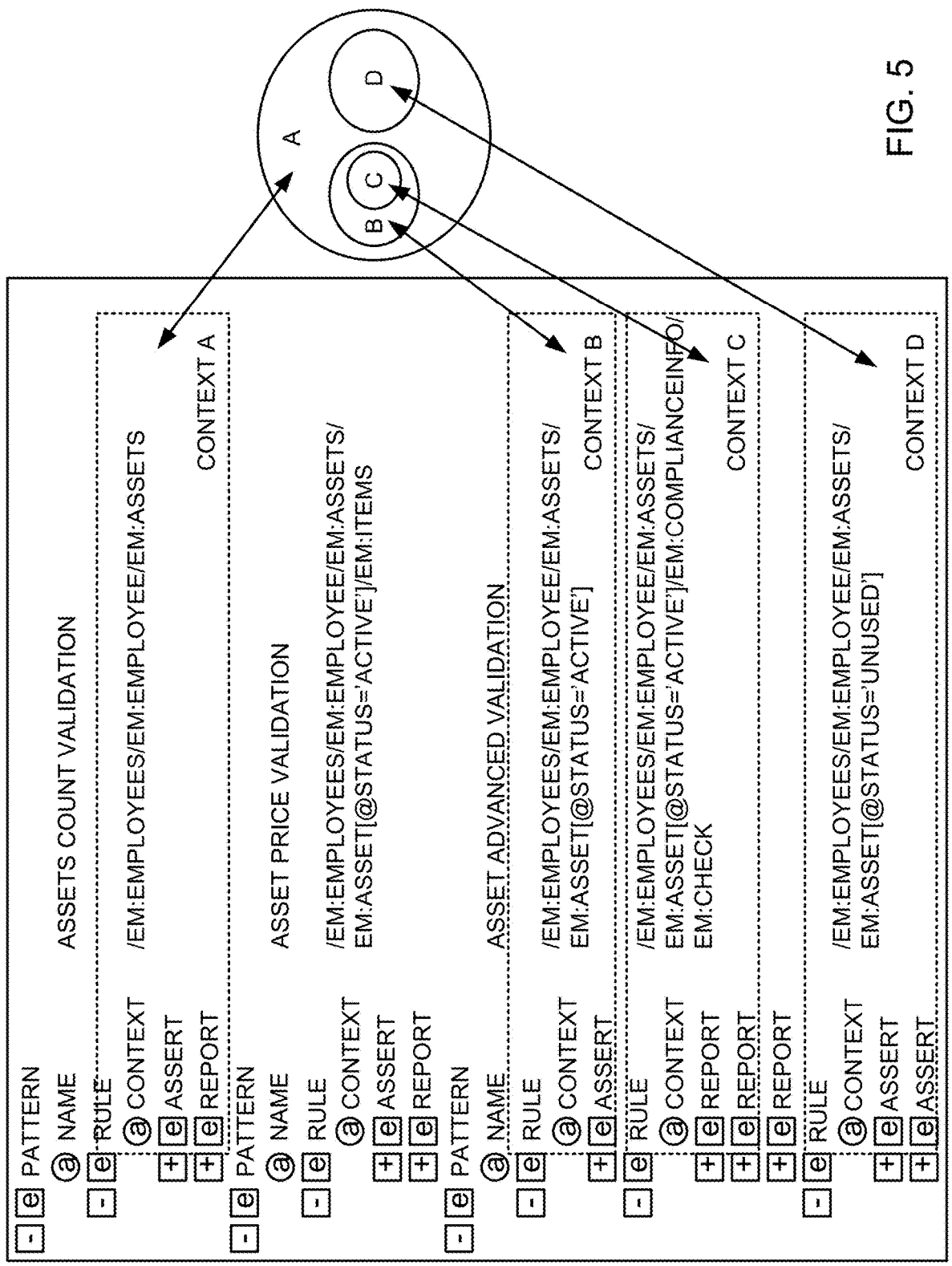
FIG. 5 illustrates an execution context according to an embodiment of the present invention.

These rule execution contexts may be marked as hierarchical and shareable. For example, in FIG. 5, context A, B, C, and D are examples of rule execution contexts that apply separately for different rules. In FIG. 5, the context A is "po: order" meaning all order elements under the root node. All rules of the rule set A are evaluated under this context (all order elements). Then the populated context A may be registered into a context registry 118 of this validation process.

The context B is ".[@orderStatus='Paid' ]", meaning those order elements that have a "paid" status. The scope of context B may be evaluated based on the scope of the context A instead of the root element of DOM tree. The scope of context C also may be evaluated based on the scope of the context B which denotes paid orders rather than all of the orders. The context A and the context B may both be extracted from the context registry of this validation process.

The rules under context A may be triggered under their execution context (all the order elements). When the Context B is populated, if there is no context hierarchy, these elements may be determine form a root node instead of from already populated order elements. According to one embodiment of the present invention, the context B population may be based on the achieved order elements (context A) instead of the whole root node, to expedite the extracting process.

A rule matcher 113 is used to evaluate the assertions of each rule under the current rule execution context. If the evaluation is false, the rule will be triggered. For example, the above rule (as following) describes that the sex and title of an employee must be consistent, the employee must have a serialNumber and department identifier (Id) and the serial number must start with the department Id.

According to one embodiment of the present invention, validation may be performed for the whole XML instance document with all or part of the rules, or validation may be performed for part of the XML instance document with all or part of the rules. After data objects to be validated and rule objects are determined, the validation process may be similar to the above process, e.g., for the data objects to be validated, to execute the rule objects in a certain execution context.

Regarding the user defined function 114, except for the native XPath function, users may extend their customized function to implement a special requirement. The user defined function 114 is used to help extract data from XML document, and also help populate the rule execution context and evaluate the assertions of the rule.

An output generator registry 115 includes different output generators that may be customized by users based on their requirements.

A user-defined output generator 116 is for output defined by a user, and is registered into the output generator registry 115 to help generate the validation report.

The validation report 117 is the final execution result of the constraints rules applied to the XML document. The result may be generated according to the user-defined output.

Figure 6:
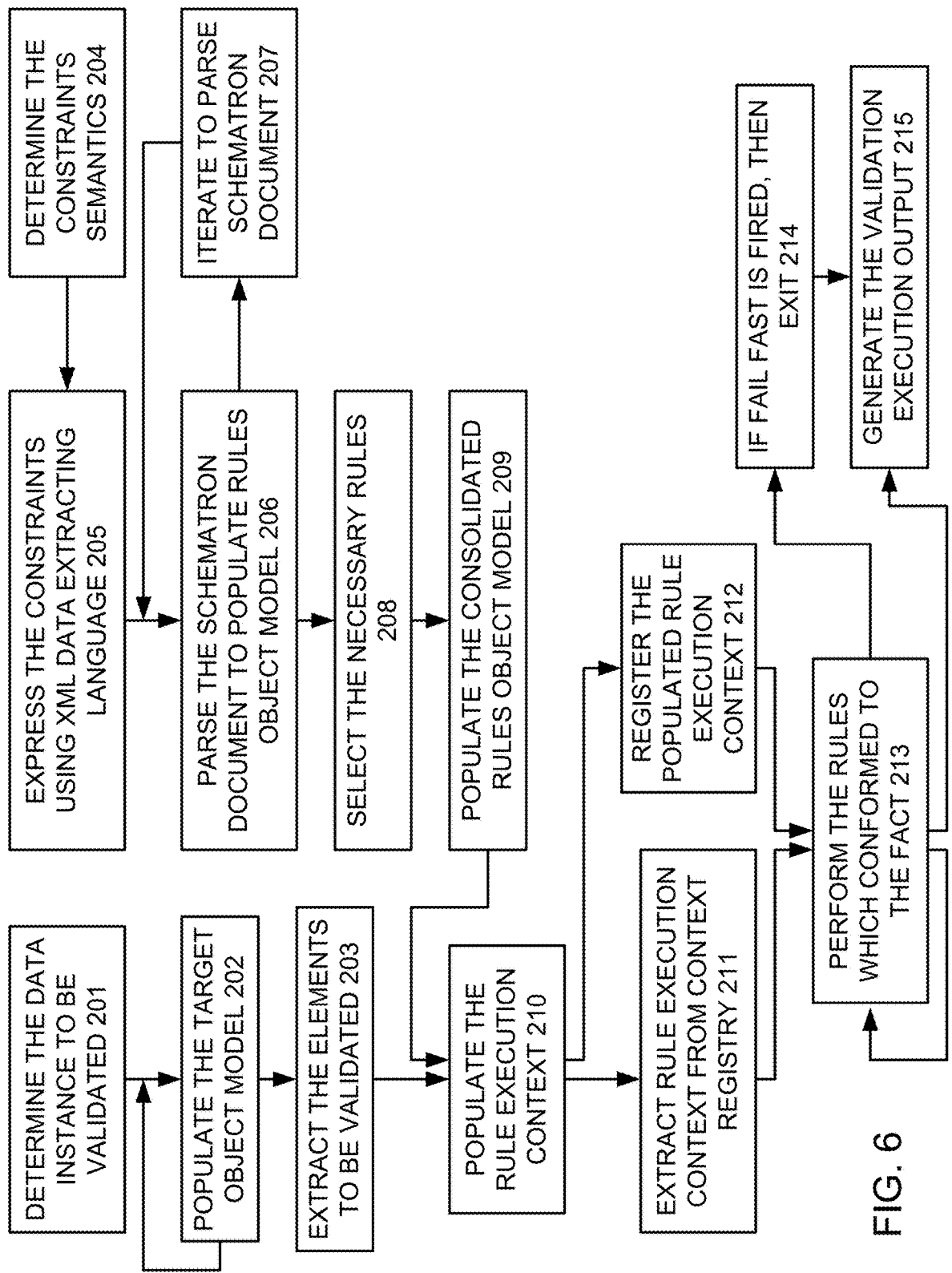
FIG. 6 illustrates a flowchart for XML document validation method according to a further embodiment of the present invention.

FIG. 6 illustrates a flowchart for an example XML document validation method according to a further embodiment of the present invention. The method includes the following steps. At step 201, determine the data instance to be validated. The XML instance document may be determined according to real requirements and application logic which contain various structure constraints or business control constraints, etc.

```
<rule context="/em:employees/em:employee">
    <assert
        test="(@sex='Male' and @title='Mr') or (@sex='Female' and (@title='Mrs' or
@title='Miss'))">
            The value of title does not match the value of sex.
    </assert>
    <assert test="@serialNumber and @deptId">
        Both serialNumber and deptId must be present.
    </assert>
    .........
</rule>
```

Then, when these assertions are to be matched, the rule matcher 113 will obtain DOM elements from the XML instance document based on an Xpath expression, e.g., the context attribute of an element rule "/em:employees/em: employee." Execution of the Xpath expression in the XML instance may obtain the following element.

```
<employee serialNumber="SOADC913247" sex="FeMale" title= "Mr"
    deptId="SOADC">
......
</employee>
```

Then, match the first assertion, execute the attribute value"(@sex='Male' and @title='Mr') or (@sex='Female' and (@title='Mrs' or @title='Miss'))" on the above obtained DOM element. If the returned value is false, then the assertion meets the condition and will be triggered with "The value of title does not match the value of sex" as a validation result output. When matching the second assertion, then execute test attribute value "@serialNumber and @deptId." The returned value is true, thus the assertion does not meet the condition and will not be triggered.

At step 202, populate the target object model. An XML parser may be used to parse XML documents based on the W3C DOM standard, represent XML data as an object tree in memory, and provide an object-oriented interface to access XML data object in the object tree.

At step 203, extract the elements, e.g., an XML data object, to be validated using user-defined data extracting criteria. The user may select the elements to be validated from a target XML document according to user-defined data extracting criteria. For example, some elements may be extracted which have a same type from a whole DOM tree, etc.

At step 204, determine the constraints semantics, e.g., determine rules for validation. Based on the above achieved XML data instance document, determine the real constraints semantics. For example, peoples' first names and last names must be alphanumeric and cannot start with a digit.

At step 205, express the constraints using XML data extracting language, e.g., XPath, etc., to form a Schematron document. These constraints semantics may be expressed using XML data extracting language, e.g. XPath 1.0. For example, a constraint about "Can contain only alphanumeric and can only start with an alphabet" may be expressed as the following XPath statement:

```
not(normalize-space(translate(.,
' ABCDEFGHIJKLMNOPQRSTUVWXYZabcdefghijklmnopqrstuvwxyz0123456789',
'*                                                                  ')))
```

At step 206, parse the Schematron document to populate the rules object model. In addition to step 205, this step parses the constraints rules document according to related different Schematron version parser, and then populates the rules object model in memory which may be used to evaluate the XML instance document.

At step 207, iterate to parse the Schematron document. If these constraints are expressed as multiple separated rules or these rules are based on different Schematron versions, then it may repeat the execution of step 206.

At step 208, select the necessary rules. If a user just needs part of the rules of the rules object model, the unused rules objects may be filtered out from the entire parsed rules object model. This step may help reduce the number of rules which may be triggered so that the execution performance may be improved. For example, if one Schematron rule document contains the WSDL elements related rules and the XSD elements related rules, and the XML instance document only contains the WSDL elements, then the XSD related rules of the Schematron document need not be triggered and thus may be filtered out. The filter rules may be based on the business semantics or defined by a user.

At step 209, populate the consolidated rules object model. Based on step 206 and step 208, a consolidated rules object model including the appropriate rules may be obtained.

At step 210, populate the rule execution context. Each rule has its execution context. This step is to help construct the context of rules and maintain the context hierarchy. To populate the rule execution context, it is first determined whether the corresponding context for the rule exists in a rule context registry; if yes, it is directly extracted for use; otherwise, the context is calculated and registered into the context registry.

A detailed procedure may be based upon the following method. Context CA, CB, CC and CD correspond to the context of a rule set A, B, C and D. For example, context CA may be expressed as "/em:employees/em:employee/em:assets", representing all the assets information under an employee element. Then, rule set A may be executed for all assets information in the context. The context may also be registered to the context registry for reuse.

Context CB may be expressed as:
"/em:employees/em:employee/em:assets/em:asset[@status='active']", representing all the assets information with active status under an employee element. Context CD may be expressed as "/em:employees/em:employee/em:assets/em:asset[@ status='unused']," representing all the assets information with unused status under an employee element. The elements in context CB and CD may be based on one subset of the context CA. Then, the context CA in the registry may be used for calculating the context CB and CD.

Context CC may be expressed as:
"/em:employees/em:employee/em:assets/em:asset[@status='active']/em:complianceInfo/em:check", representing all the assets security checking information with active status under an employee element. The elements in context CC may be based on one subset of the context CB. Then, the context CB in the registry may be used for calculating the context CC.

At step 211, extract rule execution context from the context registry. If the rule execution context has already been populated, it may be extracted from the rules execution context registry.

At step 212, register the populated rule execution context. If the rule execution context is populated for the first time, the populated execution context may be registered into the context registry for sharing and reuse.

At step 213, perform the rules which conformed to the fact. Based on the populated context from step 210, this step is to perform the concrete rules which conformed to the fact. When a policy is triggered, the corresponding output module will be triggered.

At step 214, if one rule needing fail-fast mechanism is fired (e.g., triggered), then this execution process exits.

At step 215, generate the validation execution output. According to step 213, this step is to generate the validation execution output according to a user-defined output format.

According to a further embodiment of the present invention, a system for validating an XML document is provided and includes a memory. The system includes a data parsing module configured to parse at least one XML document to be validated, and to represent XML data in the document as at least one data object model in the memory; a rule parsing module configured to parse at least one rule document and create a rule object model in the memory; an extracting module configured to extract at least part of the data objects from the data object model and extract at least part of the rule objects from the rule object model; and a validation module configured to perform validation in a corresponding context for the at least part of data objects based upon the extracted at least part of rule objects.

According to an embodiment, the rule document is a Schematron document, and rule objects in the rule object model maintain a hierarchical relationship corresponding to elements in the Schematron document.

According to an embodiment, each element in the XML document is mapped to a data object in the data object model, and the data objects maintain a hierarchical relationship corresponding to elements in the XML document to be validated.

According to an embodiment, the extracting module is configured to extract at least part of rule objects from the rule object model according to predefined rule extraction criteria.

According to an embodiment, the extracting module is configured to extract at least part of data objects from the data object model according to predefined data extraction criteria.

According to a further embodiment, the system may further comprise an execution context generating module configured to generate an execution context for at least one rule object of the extracted rule object and register the execution context to a context registry, and the validation module is configured to perform validation for the at least one rule object in the execution context.

According to yet another embodiment, the system may further include a searching module configured to search an execution context for one rule object of the extracted rule objects from a context registry, and the validation module is configured to perform validation for the one rule object in the execution context.

According to an embodiment, the extracting module is configured to extract at least part of the rule objects from the rule object model and at least part of the data objects from the data object model according to a predefined function.

According to an embodiment, the execution context generating module is configured to generate the execution context for at least one rule object according to a predefined function.

According to an embodiment, the validation module is configured to stop validation in response to a fail-fast rule being triggered.

According to embodiments of the present invention, the method and system is provided for high performance and flexible Schematron based XML validation. One embodiment of the invention leverages data extracting and context sharing. One step execution to avoid the two transformations based on XSLT may be utilized, so that performance may be improved. The context of rules is shareable, so that the rule expressions may be read easily, and the execution scope of a rule may be reduced. Then the performance of rule execution may be improved. In one embodiment of the invention, the shareable rule execution context is the concrete execution scope of each rule applied to the XML instance document. These rule execution contexts may be marked as hierarchical and shareable.

According to an embodiment of the invention, based on an in-memory rule object model and extended validation engine, the fail-fast Schematron validation with high performance may be achieved. The foundational XML data extracting and XML parser may be used to implement the fail-fast mechanism. The XSLT based implementation continues to execute the transformation process in spite of the real execution situation.

According to an embodiment of the invention, a rule execution engine is optimized with sharable context and accurate rule matching.

According to an embodiment of the invention, a flexible mechanism is provided for partial validation by leveraging an in-memory rule object model and XML data model for data and rule extracting to use user-defined target XML elements set and fine grained units in Schematron document (rule and assertion). For example, a legacy system includes one previous Schematron compliant with version 1.5, while the newly-created Schematron document which uses the ISO Schematron version leverages the legacy Schematron 1.5 rules. In this situation, the hybrid Schematron versions may work together. It may impose a challenge to accommodate with the hybrid Schematron rules which use different Schematron versions for XSLT based Schematron implementation.

Flexible validation may be provided using selected fine grained units of Schematron document. If a user just needs part of the rules object model, the unused rules objects may be filtered out from the entire parsed rules object model. This step may help reduce the rules that will be triggered so that the execution performance may be improved. For example, if one Schematron rule document includes WSDL elements related rules and XSD elements related rules, and the XML instance document only contains the WSDL elements, the XSD related rules of the Schematron document may be filtered out. The filter rules may be based on the business semantics or may be defined by a user.

The present invention also provides a storage media, which comprises instructions for carrying out the method according to the invention.

While the invention has been illustrated and described by referring specifically to the preferred embodiments, those skilled in the art will understand that various changes may be made thereto both in form and detail without departing from the spirit and scope of the invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art based upon the present description without departing from the scope and spirit of the invention. The embodiment was chosen and described to explain the principles of the invention and the practical application, and to enable others of ordinary skill in the art to understand the invention for various embodiments with various modifications as suitable for a particular use contemplated.

What claimed is:

1. A method for validating an XML document, comprising:
   reading, by an XML parser of a validation engine, the XML document inputted into the XML parser, wherein said XML parser provides programmatic access to XML data of the XML document and determines how the XML data is accessed and retrieved;
   parsing, by the XML parser, at least part of the XML document to be validated and expressing the XML data in the at least part of the XML document as data objects in at least one data object model in a memory, wherein the XML document being parsed is modeled as a node-labeled tree;
   mapping each element of the XML document parsed by the XML parser to a sub tree of the node-labeled tree, wherein each root node of each sub tree is labelled with a tag describing an element of the sub tree;
   parsing, by a rule parser of the validation engine, at least part of a rule document inputted into the rule parser, the rule document comprising one or more elements in a hierarchical relationship and outputting rule data parsed from the at least part of the rule document as scoped rule objects in a rule object model in the memory, wherein the rule object data model maintains the hierarchical relationship of the one or more elements;

selecting, by a user interface of the validation engine, one or more element of the XML document mapped to at least one sub tree of the node-labeled tree for validation;

extracting, the selected one or more element of the XML document from the at least one sub tree and extracting at least part of the scoped rule objects from the rule object model;

populating, by a rule context populator of the validation engine, a rule execution context providing a rule execution scope of each rule applied to the one or more element of the XML document selected for validation, wherein the rule execution context supports a fail-fast implementation; and validating the one or more element of the XML document selected for validation by executing the scoped rule objects extracted from the rule object data model under the rule execution context.

2. The method of claim 1, where the at least part of the rule document comprises a subset of a "phase" element of the rule document, and where the subset of the "phase" element comprises one of a rule or an assertion that respectively specifies the rule execution scope of at least one of the subset of the scoped rule objects.

3. The method of claim 1, where the at least part of the rule document comprises a hybrid Schematron rule that is a subset of a "phase" element that is based upon multiple Schematron versions, and where the subset of the "phase" element specifies the rule execution scope of at least one of the subset of the scoped rule objects.

4. The method of claim 1, where the scoped rule objects comprise sharable rule execution contexts reusable during execution by different scoped rule objects.

5. The method of claim 1, wherein validating the one or more element of the XML document comprises executing a subset of the scoped rule objects hierarchically within a shared rule execution context.

6. The method of claim 1, further comprising:
generating an execution context for at least one scoped rule object according to a predefined function, registering the execution context to a context registry, and performing validation of the at least one scoped rule object in the execution context.

7. The method of claim 1, where:
the rule document comprises a Schematron document and the scoped rule objects in the rule object model maintain a hierarchical relationship within the memory according to a hierarchical relationship of corresponding elements in the Schematron document; and
the data objects maintain a hierarchical relationship within the memory according to a hierarchical relationship of corresponding elements in the XML document.

8. A system for validating an XML document, comprising:
a memory; and
a processor programmed to:
read, by an XML parser of a validation engine, the XML document inputted into the XML parser, wherein said XML parser provides programmatic access to XML data of the XML document and determines how the XML data is accessed and retrieved;
parse, by the XML parser, at least part of the XML document to be validated and express the XML data in the at least part of the XML document as data objects in at least one data object model in the memory, wherein the XML document being parsed is modeled as a node-labeled tree;

map each element of the XML document parsed by the XML parser to a sub tree of the node-labeled tree, wherein each root node of each sub tree is labelled with a tag describing an element of the sub tree;

parse, by a rule parser of the validation engine, at least part of a rule document inputted into the rule parser, the rule document comprising one or more elements in a hierarchical relationship and output rule data parsed from the at least part of the rule document as scoped rule objects in a rule object model in the memory, wherein the rule object data model maintains the hierarchical relationship of the one or more elements;

select, by a user interface of the validation engine, one or more element of the XML document mapped to at least one sub tree of the node-labeled tree for validation;

extract, the selected one or more element of the XML document from the at least one sub tree and extracting at least part of the scoped rule objects from the rule object model;

populate, by a rule context populator of the validation engine, a rule execution context providing a rule execution scope of each rule applied to the one or more element of the XML document selected for validation, wherein the rule execution context supports a fail-fast implementation; and validate the one or more element of the XML document selected for validation by executing the scoped rule objects extracted from the rule object data model under the rule execution context.

9. The system of claim 8, where the at least part of the rule document comprises a subset of a "phase" element of the rule document, and where the subset of the "phase" element comprises one of a rule or an assertion that respectively specifies the rule execution scope of at least one of the subset of the scoped rule objects.

10. The system of claim 8, where the at least part of the rule document comprises a hybrid Schematron rule that is a subset of a "phase" element that is based upon multiple Schematron versions, and where the subset of the "phase" element specifies the rule execution scope of at least one of the subset of the scoped rule objects.

11. The system of claim 8, where the scoped rule objects comprise sharable rule execution contexts reusable during execution by different scoped rule objects.

12. The system of claim 8, where, in being programmed to validate, the processor is programmed to execute a subset of scoped rule objects hierarchically within a shared rule execution context.

13. The system of claim 8, where the processor is further programmed to:
generate an execution context for at least one scoped rule object according to a predefined function, register the execution context to a context registry, and perform validation of the at least one scoped rule object in the execution context.

14. The system of claim 8, where:
the rule document comprises a Schematron document and the scoped rule objects in the rule object model maintain a hierarchical relationship within the memory according to a hierarchical relationship of corresponding elements in the Schematron document; and
the data objects maintain a hierarchical relationship within the memory according to a hierarchical relationship of corresponding elements in the XML document.

15. A computer program product comprising a non-transitory computer readable storage medium including a computer readable program code, where the computer readable program code when executed on a computer causes the computer to:

read, by an XML parser of a validation engine, the XML document inputted into the XML parser, wherein said XML parser provides programmatic access to XML data of the XML document and determines how the XML data is accessed and retrieved;

parse, by the XML parser, at least part of the XML document to be validated and express the XML data in the at least part of the XML document as data objects in at least one data object model in a memory, wherein the XML document being parsed is modeled as a node-labeled tree;

map each element of the XML document parsed by the XML parser to a sub tree of the node-labeled tree, wherein each root node of each sub tree is labelled with a tag describing an element of the sub tree;

parse, by a rule parser of the validation engine, at least part of a rule document inputted into the rule parser, the rule document comprising one or more elements in a hierarchical relationship and output rule data parsed from the at least part of the rule document as scoped rule objects in a rule object model in the memory, wherein the rule object data model maintains the hierarchical relationship of the one or more elements;

select, by a user interface of the validation engine, one or more element of the XML document mapped to at least one sub tree of the node-labeled tree for validation;

extract, the selected one or more element of the XML document from the at least one sub tree and extracting at least part of the scoped rule objects from the rule object model;

populate, by a rule context populator of the validation engine, a rule execution context providing a rule execution scope of each rule applied to the one or more element of the XML document selected for validation, wherein the rule execution context supports a fail-fast implementation; and validate the one or more element of the XML document selected for validation by executing the scoped rule objects extracted from the rule object data model under the rule execution context.

16. The computer program product of claim 15, where the at least part of the rule document comprises a subset of a "phase" element of the rule document, and where the subset of the "phase" element comprises one of a rule or an assertion that respectively specifies the rule execution scope of at least one of the subset of the scoped rule objects.

17. The computer program product of claim 15, where the at least part of the rule document comprises a hybrid Schematron rule that is a subset of a "phase" element that is based upon multiple Schematron versions, and where the subset of the "phase" element specifies the rule execution scope of at least one of the subset of the scoped rule objects.

18. The computer program product of claim 15, where the scoped rule objects comprise sharable rule execution contexts reusable during execution by different scoped rule objects.

19. The computer program product of claim 15, where, in causing the computer to validate the one or more element of the XML document, the computer readable program code when executed on the computer causes the computer to execute a subset of scoped rule objects hierarchically within a shared rule execution context.

20. The computer program product of claim 15, where the computer readable program code when executed on the computer further causes the computer to:

generate an execution context for at least one scoped rule object according to a predefined function, register the execution context to a context registry, and perform validation of the at least one scoped rule object in the execution context.

21. The computer program product of claim 15, where:
the rule document comprises a Schematron document and the scoped rule objects in the rule object model maintain a hierarchical relationship within the memory according to a hierarchical relationship of corresponding elements in the Schematron document; and
the data objects maintain a hierarchical relationship within the memory according to a hierarchical relationship of corresponding elements in the XML document.

* * * * *